(12) United States Patent
Rosinger et al.

(10) Patent No.: US 9,232,791 B2
(45) Date of Patent: Jan. 12, 2016

(54) PLANT GROWTH REGULATOR

(75) Inventors: Christopher Hugh Rosinger, Hofheim (DE); Frank Ziemer, Kriftel (DE)

(73) Assignee: Bayer Intellectual Property GmbH, Monheim (DE)

( * ) Notice: Subject to any disclaimer, the term of this patent is extended or adjusted under 35 U.S.C. 154(b) by 602 days.

(21) Appl. No.: 12/330,916

(22) Filed: Dec. 9, 2008

(65) Prior Publication Data

US 2010/0009852 A1 Jan. 14, 2010

(30) Foreign Application Priority Data

Jul. 9, 2008 (EP) .................................... 08012408

(51) Int. Cl.
*A01N 37/18* (2006.01)
*A01N 41/06* (2006.01)
*A01N 31/08* (2006.01)
*A01N 47/10* (2006.01)

(52) U.S. Cl.
CPC ................ *A01N 41/06* (2013.01); *A01N 31/08* (2013.01); *A01N 47/10* (2013.01)

(58) Field of Classification Search
CPC .............................. A01N 31/08; A01N 47/10
USPC ........................................................ 504/333
See application file for complete search history.

(56) References Cited

U.S. PATENT DOCUMENTS

| 5,215,570 | A * | 6/1993 | Burckhardt et al. ........... 504/104 |
| 2005/0233904 | A1* | 10/2005 | Hills et al. ..................... 504/102 |
| 2007/0124839 | A1 | 5/2007 | Schulz et al. |
| 2007/0265164 | A1 | 11/2007 | Bartsch et al. |

FOREIGN PATENT DOCUMENTS

| DE | CA2305313 | * | 4/1999 | ............ C07C 311/51 |
| DE | WO 99/16744 | * | 4/1999 | ............ C07C 311/51 |
| WO | WO 2005/107466 | | 11/2005 | |
| WO | WO 2006/007981 | | 1/2006 | |
| WO | WO 2007/062737 | | 6/2007 | |

OTHER PUBLICATIONS

Abu-Qare et al. (Herbicide safeners: Uses, limitations, metabolism, and mechanisms of action, Chemosphere 48 (2002) p. 965-974).*
Truelove et al., Mefluidide Effects on Growth of Corn (*Zea mays*) and the Synthesis of Protein by Cucumber (*Cucumis sativus*) Cotyledon Tissue, Weed Science, Jul. 1977, 360-363, vol. 25, No. 4.

* cited by examiner

Primary Examiner — Johann R Richter
Assistant Examiner — Danielle Sullivan
(74) Attorney, Agent, or Firm — Frommer Lawrence & Haug

(57) ABSTRACT

The invention relates to the use of one or more acylsulfonamide safener compounds of formula (I):

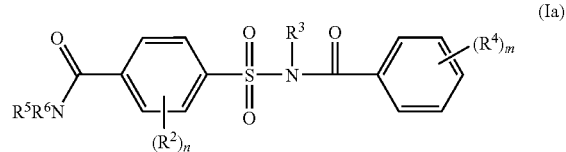

for modifying plant development of useful plants. The use provides an increase in root growth and/or a regulation in shoot growth of the plants.

21 Claims, 1 Drawing Sheet

Active substance treatment in glasshouse pot trial
(1 seed treatment, 2 below seed, 3 above seed, 4 untreated)
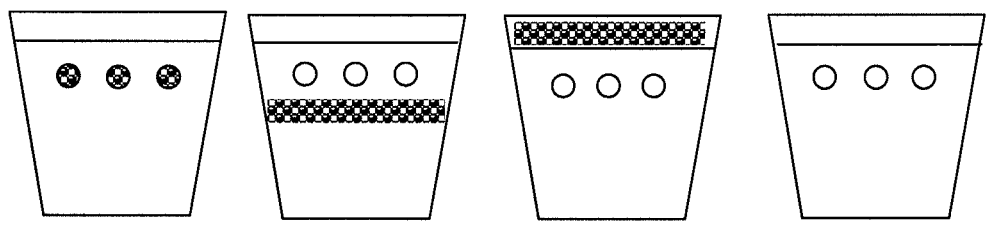

PLANT GROWTH REGULATOR

The invention relates to the field of plant protection, more specifically to the use of agrochemicals for increasing the plant health or plant growth of useful plants.

Various types of agrochemicals, such as herbicides, insecticides and fungicides, are used in crop protection to control plant diseases in crop plants. Other agrochemicals, such as typical plant growth regulators, are used to increase or improve the growth of plants and may thus increase the yield of crop plants or of specific fruits of the crop plants.

Some agrochemicals can reduce crop injury when used in association with pesticides. These compounds are called "safeners" or "antidotes" and are widely used in crop protection, particularly in the field of weed control during application of herbicides in crops. The mode of action of safeners is often not known in detail and their efficacy generally depends on the specific pesticide to be combined with.

Many safeners enhance or promote a natural defense mechanism of plants. So it is known that plants react with specific or unspecific defense mechanisms to natural stress conditions, such as, for example, chill, heat, drought, wounding, pathogen attack (viruses, bacteria, fungi, insects) and the like, but also to herbicides [Pflanzenbiochemie, pp. 393-462, Spektrum Akademischer Verlag, Heidelberg, Berlin, Oxford, Hans W. Heldt, 1996.; Biochemistry and Molecular Biology of Plants, pp.1102-1203, American Society of Plant Physiologists, Rockville, Md., eds. Buchanan, Gruissem, Jones, 2000].

It is already known that some safeners may have other beneficial effects on crop plants. WO 2006/007981 teaches that some safeners may generally increase the resistance against biotic stress.

It is also known that some safeners are within the group of compounds which can also increase the tolerance of plants to abiotic stress factors acting on this plant, such as, for example, temperature (such as chill, frost or heat), water (such as dryness, drought or anoxia), or the chemical load (such as lack of or excess of mineral salts, heavy metals, gaseous noxious substances) by increasing the expression of plant-endogenous proteins (see e. g. WO 2007/062737)

Now it has been found that compounds of a specific chemical class which are known for their safening effects surprisingly cause effects on the development of useful plants that are beneficial to the health of the crop plants.

One object of the invention is the use of one or more compounds selected from the group consisting of acylsulfonamide safeners ("Compounds (A)") for modifying plant development of useful plants, preferably as a plant growth regulator by improving root growth and/or regulating shoot growth of useful plants.

The use of the Compounds (A) according to the invention can be accomplished, for instance, by applying the compounds to the locus of the useful plants, for example to the seed, stem, foliage and/or other parts of the plants and/or the growing medium of the plants.

The term "improving root growth" means generally the increase in root growth, thus effecting one or more of the following effects, always compared to untreated useful plants:

An increase in total root mass, an increase in the average length of roots, an increase in the average thickness of roots, an increase in the speed of root growth and also an increase in secondary roots (e. g. increaso also number of roots).

A result of the improved root growth according to the invention can be a more stable plant stands, a better uptake of water and nutrition by the roots and thus a better general growth or better yield of the useful plants.

Another object of the invention is thus the use of Compounds (A) for improving the stable plant stands of useful plants or for improving the uptake of water and nutrition of useful plants, or for improving the growth or yield of useful plants.

Another effect for modifying the plant development is a more indirect or independent result of the improved root growth effect and also improves the more stable stand of plants and/or the yield of the plants.

So, the application of one or more Compounds (A) to the locus of the useful plants generally causes a valuable stem shortening of the plants.

The stem reduction stabilises the stand of the plant, especially if the stem diameter is not likewise reduced, and Compounds (A) can be used as a culm stabilizer (specific plant growth regulator) for improving the stand of a plant and thus avoiding lodging injury of the plants, especially early lodging injury of the plants.

The stem reduction also improves the nutrition uptake for other plant organs and thus the yield of the other plant organs or fruit of the plants.

Compounds (A) thus can also be used as plant growth regulator for improving the yield of the plants.

The term "Compounds (A)" are selected from the group of so-called "acylsulfonamide safeners" which are known, for example, from WO-A-97/45016, WO-A-99/16744 and EP-A-365484 and references cited therein. Preferred Compounds (A) are compounds of the formula (I) or salts thereof,

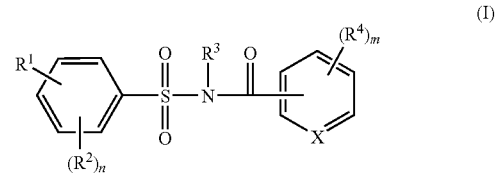

wherein

X is CH or N;

$R^1$ is —CO—$NR^5R^6$, —NH—CO—$R^7$ or —NH—CO—$NR^8R^9$, $(R^2)_n$ is a radical $R^2$ if n is 1 or represents n radicals $R^2$ attached to different carbon ring atoms of the basic ring if n is more than 1, wherein each $R^2$ independently of one another is halogen, $(C_1-C_4)$haloalkyl, $(C_1-C_4)$haloalkoxy, nitro, $(C_1-C_4)$alkyl, $(C_1-C_4)$alkoxy, $(C_1-C_4)$alkylsulfonyl, $[(C_1-C_4)alkoxy]carbonyl$ or $[(C_1-C_4)alkyl]carbonyl$, $R^3$ is hydrogen, $(C_1-C_4)$alkyl, $(C_2-C_4)$alkenyl or $(C_2-C_4)$alkinyl, $(R^4)_m$ is a radical $R^4$ if m is 1 or represents m radicals $R^4$ attached to different carbon ring atoms of the basic ring if m and is more than 1, wherein each $R^4$ independently of one another is halogen, nitro, $(C_1-C_4)$alkyl, $(C_1-C_4)$haloalkyl, $(C_1-C_4)$haloalkoxy, $(C_3-C_6)$cycloalkyl, phenyl, $(C_1-C_4)$alkoxy, cyano, $(C_1-C_4)$alkylthio, $(C_1-C_4)$alkylsulfinyl, $(C_1-C_4)$alkylsulfonyl, $[(C_1-C_4)alkoxy]carbonyl$ or $[(C_1-C_4)alkyl]carbonyl$;

$R^5$ is hydrogen, $(C_1-C_6)$alkyl, $(C_3-C_6)$cycloalkyl, $(C_2-C_6)$alkenyl, $(C_2-C_6)$alkinyl, $(C_5-C_6)$cycloalkenyl, phenyl or a 3- to 6-membered heterocyclyl having 1 to 3 heteroatoms selected from the group consisting of nitrogen, oxygen and sulfur, wherein each of the last-mentioned 7 radicals is unsubstituted or substituted by 1, 2 or 3 radicals selected from the group consisting of halogen, $(C_1-C_6)$alkoxy, $(C_1-$ $C_6$)haloalkoxy, ($C_1$-$C_2$)alkylsulfinyl, ($C_1$-$C_2$)alkylsulfonyl, ($C_3$-$C_6$)cycloalkyl, ($C_1$-$C_4$)alkoxycarbonyl, [($C_1$-$C_4$)alkyl]carbonyl and phenyl and, in case of cyclic basic radicals, also ($C_1$-$C_4$)alkyl and ($C_1$-$C_4$)haloalkyl, $R^6$ is hydrogen, ($C_1$-$C_6$)alkyl, ($C_3$-$C_6$)cycloalkyl, ($C_2$-$C_6$)alkenyl or ($C_2$-$C_6$)alkinyl, each of the last-mentioned 3 radicals is unsubstituted or substituted by 1, 2 or 3 radicals selected from the group consisting of halogen, hydroxyl, ($C_1$-$C_4$)alkyl, ($C_1$-$C_4$)alkoxy and ($C_1$-$C_4$)alkylthio, or $R^5$ and $R^6$ together with the nitrogen atom attached to represent pyrrolidin-1-yl- or piperidin-1-yl, $R^7$ is hydrogen, ($C_1$-$C_6$)alkyl, ($C_3$-$C_6$)cycloalkyl, wherein each of the last-mentioned 2 radicals is unsubstituted or substituted by 1, 2 or 3 radicals selected from the group consisting of halogen, ($C_1$-$C_4$)alkoxy, ($C_1$-$C_6$)haloalkoxy and ($C_1$-$C_4$)alkylthio and, in case of cyclic basic radicals, also ($C_1$-$C_4$)alkyl and ($C_1$-$C_4$)haloalkyl, $R^8$ is hydrogen, ($C_1$-$C_8$)alkyl, ($C_2$-$C_6$)alkenyl, ($C_2$-$C_6$)alkinyl or ($C_3$-$C_8$)cycloalkyl, wherein each of the last-mentioned 4 radicals is unsubstituted or substituted by 1, 2 or 3 radicals selected from the group consisting of halogen, ($C_1$-$C_4$)alkoxy, ($C_1$-$C_6$)haloalkoxy and ($C_1$-$C_4$)alkylthio and, in case of cyclic basic radicals, also ($C_1$-$C_4$)alkyl and ($C_1$-$C_4$)haloalkyl, $R^9$ is hydrogen, ($C_1$-$C_8$)alkyl, ($C_2$-$C_6$)alkenyl, ($C_2$-$C_6$)alkinyl or ($C_3$-$C_8$)cycloalkyl, wherein each of the last-mentioned 4 radicals is unsubstituted or substituted by 1, 2 or 3 radicals selected from the group consisting of halogen, ($C_1$-$C_4$)alkoxy, ($C_1$-$C_6$)haloalkoxy and ($C_1$-$C_4$)alkylthio and, in case of cyclic basic radicals, also ($C_1$-$C_4$)alkyl and ($C_1$-$C_4$)haloalkyl, n is 0, 1, 2, 3 or 4, preferably 0, 1 or 2, and
m is 0, 1, 2, 3 or 4, preferably 1 or 2.

More preferred Compounds (A) are compounds of the formula (Ia) or salts thereof,

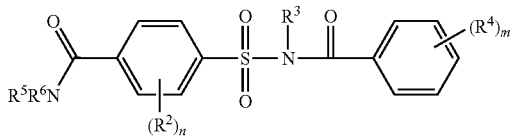

(Ia)

wherein $(R^2)_n$, $R^3$, $(R^4)_m$, $R^5$, $R^6$ n and m are defined as for formula (I), and preferably wherein
$R^3$ is hydrogen,
$(R^4)_m$ is a radical $R^4$ if m is 1 or represents m radicals $R^4$ attached to different carbon ring atoms of the basic ring if m and is more than 1, wherein each $R^4$ independently of one another is halogen, methyl, ethyl, n-propyl, i-propyl, $CF_3$, ($C_1$-$C_4$)haloalkoxy or ($C_1$-$C_4$)alkoxy,
$R^5$ is ($C_1$-$C_6$)alkyl or ($C_3$-$C_6$)cycloalkyl, wherein each of the last-mentioned 2 radicals is unsubstituted or substituted by 1, 2 or 3 radicals selected from the group consisting of halogen, ($C_1$-$C_4$)alkoxy, ($C_1$-$C_4$)haloalkoxy, ($C_1$-$C_2$)alkylsulfinyl, ($C_1$-$C_2$)alkylsulfonyl, ($C_3$-$C_6$)cycloalkyl, ($C_1$-$C_4$)alkoxycarbonyl and [($C_1$-$C_2$)alkyl]carbonyl and, in case of cyclic basic radicals, also ($C_1$-$C_4$)alkyl and ($C_1$-$C_4$)haloalkyl,
$R^6$ is hydrogen or ($C_1$-$C_4$)alkyl, preferably hydrogen,
m is 0, 1 or 2, preferably 1 or 2, and
n is zero.

More preferred compounds of the formula (Ia) or salts thereof are those wherein $R^3$ is hydrogen, and
$(R^4)_m$ is 2-methoxy and $R^5$ is cyclopropyl or
$(R^4)_m$ is 5-chloro-2-methoxy and $R^5$ is cyclopropyl or
$(R^4)_m$ is 2-methoxy and $R^5$ is ethyl or
$(R^4)_m$ is 5-chloro-2-methoxy and $R^5$ is isopropyl or
$(R^4)_m$ is 2-methoxy and $R^5$ is isopropyl, and
$R^6$ is hydrogen, and
n is zero.

Such compounds are known from WO 99/16744.
Most preferred compound of the formula (Ia) or salts thereof is the compound wherein
$R^3$ is hydrogen,
$(R^4)_m$ is 2-methoxy,
$R^5$ is cyclopropyl,
$R^6$ is hydrogen, and
n is zero
(common name "cyprosulfamide").

Also preferred Compounds (A) are compounds of the formula (Ib) or salts thereof,

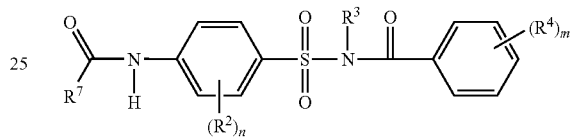

(Ib)

wherein $(R^2)_n$, $R^3$, $(R^4)_m$, $R^7$, n and m are defined as for formula (I), and preferably wherein
$R^3$ is hydrogen,
$(R^4)_m$ is a radical $R^4$ if m is 1 or represents m radicals $R^4$ attached to different carbon ring atoms of the basic ring if m and is more than 1, wherein each $R^4$ independently of one another is halogen, ($C_1$-$C_4$)alkyl, $CF_3$, ($C_1$-$C_4$)haloalkoxy or ($C_1$-$C_4$)alkoxy,
$R^7$ is ($C_1$-$C_6$)alkyl or ($C_3$-$C_6$)cycloalkyl, wherein each of the last-mentioned 2 radicals is unsubstituted or substituted by 1, 2 or 3 radicals selected from the group consisting of halogen, ($C_1$-$C_4$)alkoxy, ($C_1$-$C_6$)haloalkoxy and ($C_1$-$C_4$)alkylthio und and, in case of cyclic basic radicals, also ($C_1$-$C_4$)alkyl and ($C_1$-$C_4$)haloalkyl,
m is 0, 1 or 2, preferably 1 or 2, and
n is zero.

Such compounds are known from WO 99/16744.
Also preferred Compounds (A) are compounds of the above formula (Ic) or salts thereof,

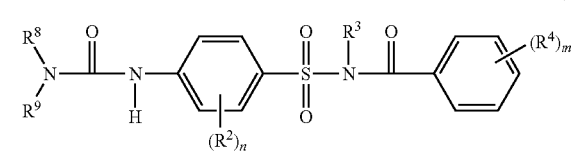

(Ic)

wherein $(R^2)_n$, $R^3$, $(R^4)_m$, $R^8$, $R^9$, n and m are defined as for formula (I), and preferably wherein
$R^3$ is hydrogen,
$(R^4)_m$ is a radical $R^4$ if m is 1 or represents m radicals $R^4$ attached to different carbon ring atoms of the basic ring if m and is more than 1, wherein each $R^4$ independently of one another is halogen, ($C_1$-$C_4$)alkyl, $CF_3$, ($C_1$-$C_4$)haloalkoxy or ($C_1$-$C_4$)alkoxy, preferably halogen, ($C_1$-$C_4$)alkyl, $CF_3$ or ($C_1$-$C_4$)alkoxy $R^8$ is hydrogen, $(C_1-C_8)$alkyl, $(C_2-C_6)$alkenyl, $(C_2-C_6)$alkinyl or $(C_3-C_8)$cycloalkyl, $R^9$ is hydrogen, $(C_1-C_8)$alkyl, $(C_2-C_6)$alkenyl, $(C_2-C_6)$alkinyl or $(C_3-C_8)$cycloalkyl, m is 0, 1 or 2, preferably 1 or 2, and n is zero.

Such compounds are known from EP-A-365484, for instance specifically

1-[4-(N-2-methoxybenzoylsulfamoyl)phenyl]-3-methyl-urea,

1-[4-(N-2-methoxybenzoylsulfamoyl)phenyl]-3,3-dimethyl-urea,

1-[4-(N-4,5-dimethylbenzoylsulfamoyl)phenyl]-3-methyl-urea.

By addition of a suitable inorganic or organic acid, such as, for example, HCl, HBr, $H_2SO_4$ or $HNO_3$, but also oxalic acid or sulfonic acids, onto a basic group, such as, for example, amino or alkylamino, the compounds of the formula (I) may form salts. Suitable substituents present in deprotonated form, such as, for example, sulfonic acids or carboxylic acids, may form inner salts with groups which for their part can be protonated, such as amino groups. Salts may also be formed by replacing the hydrogen of suitable substituents, such as, for example, sulfonic acids or carboxylic acids, or the acidic hydrogen atom of a —$SO_2NHCO$— group by an agriculturally suitable cation. These salts are, for example, metal salts, in particular alkali metal salts or alkaline earth metal salts, especially sodium salts and potassium salts, or else ammonium salts, salts with organic amines or quaternary ammonium salts.

In the present patent specification, including the accompanying claims, the aforementioned substituents have the following meanings:

Halogen means fluorine, chlorine, bromine or iodine.

The term "halo" before the name of a radical means that this radical is partially or completely halogenated, that is to say substituted by F, Cl, Br or I in any combination.

The expression "$(C_1-C_6)$alkyl" means an unbranched or branched non-cyclic saturated hydrocarbon radical having 1, 2, 3, 4, 5 or 6 carbon atoms (indicated by a range of C-atoms in the parenthesis), such as, for example a methyl, ethyl, propyl, isopropyl, 1-butyl, 2-butyl, 2-methylpropyl or tert-butyl radical. The same applies to alkyl groups in composite radicals such as "alkoxyalkyl".

Alkyl radicals and also in composite groups, unless otherwise defined, preferably have 1 to 4 carbon atoms.

"$(C_1-C_6)$Haloalkyl" means an alkyl group mentioned under the expression "$(C_1-C_6)$alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$[(C_1-C_4)$alkoxy]$(C_1-C_6)$alkyl" means $(C_1-C_6)$alkyl which is substituted by one or more $(C_1-C_4)$alkoxy groups, preferably by one $(C_1-C_4)$alkoxy group.

"$(C_1-C_6)$Alkoxy" means an alkoxy group whose carbon chain has the meaning given under the expression "$(C_1-C_6)$alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$Alkenyl" means an unbranched or branched non-cyclic carbon chain having a number of carbon atoms which corresponds to this stated range and which contains at least one double bond which can be located in any position of the respective unsaturated radical. "$(C_2-C_6)$alkenyl" accordingly denotes, for example, the vinyl, allyl, 2-methyl-2-propenyl, 2-butenyl, pentenyl, 2-methylpentenyl or the hexenyl group.

"$(C_2-C_6)$alkynyl" means an unbranched or branched non-cyclic carbon chain having a number of carbon atoms which corresponds to this stated range and which contains one triple bond which can be located in any position of the respective unsaturated radical. "$(C_2-C_6)$alkynyl" accordingly denotes, for example, the propargyl, 1-methyl-2-propynyl, 2-butynyl or 3-butynyl group.

"$(C_3-C_6)$cycloalkyl" denotes monocyclic alkyl radicals, such as the cyclopropyl, cyclobutyl, cyclopentyl or cyclohexyl radical.

"$(C_4-C_6)$cycloalkenyl" denotes a carbocyclic, nonaromatic, partially unsaturated ring having 4 to 6 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl.

The expression "one or more radicals selected from the group consisting of" in the definition is to be understood as meaning in each case one or more identical or different radicals selected from type of radicals defined, unless specific limitations are defined expressly.

The Compounds (A) are known for reducing phytotoxic side-effects of selective herbicides on crop plants. Their beneficial effects on the development of useful plants have not been known before.

While the safening effects of Compounds (A) are normally observed if a Compound (A) is applied together with a pesticide, preferably herbicide, it is not needed to have a pesticide applied together with the Compound (A) when applying the safener according to the use of the invention.

The term "useful plants" generally means crops of plants common in agriculture or horticulture. Preferred are agriculturally useful plants, plantation plants and ornamental plants.

More preferred are plants of economically important crops such as, for example, wheat, barley, rye, triticale, millet, rice, maize (corn), sorghum, oats, sugar beet, cotton, sugar cane or soybeans, particularly wheat, barley, rice, maize (corn) or sorghum, more particularly maize (corn).

Also preferred are plants of plantation crops such as oil palm, coconut palm, India-rubber tree, citrus, pineapples, pome, cotton, coffee, cocoa and the like, as well as plants in fruit production and viticulture.

Generally, the plants can be naturally occurring varieties of crop plants, cultivated crop plants, crop plants modified by mutagenation or genetic engineering or to be developed cultivated novel crop plants.

Traditional ways of generating novel plants which have modified characteristics in comparison with existing plants consist, for example, in traditional breeding methods and the generation of mutants. However, it is also possible to generate novel plants with altered characteristics with the aid of genetic engineering methods (see, for example, EP-A-0221044, EP-A-0131624). For example, several cases have been described of genetic engineering modifications of crop plants with the purpose of modifying the starch synthesized in the plants (for example WO 92/11376, WO 92/14827, WO 91/19806), transgenic crop plants which are resistant to certain herbicides of the glufosinate type (cf., for example, EP-A-0242236, EP-A-242246) or the glyphosate type (WO 92/00377) or the sulfonylurea type (EP-A-0257993, U.S. Pat. No. 5,013,659), transgenic crop plants, for example cotton, which are capable of producing Bacillus thuringiensis toxins (Bt toxins) which make the plants resistant to specific pests (EP-A-01 42924, EP-A-01 93259), transgenic crop plants whose fatty acid spectrum is modified (WO 91/13972).

A large number of techniques in molecular biology by means of which novel transgenic plants with altered characteristics can be generated are known in principle; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423-431).

In order to perform such genetic engineering manipulations, nucleic acid molecules may be introduced into plasmids which allow mutagenesis or a sequence change by means of recombination of DNA sequences. It is possible, for example, with the aid of the abovementioned standard methods to perform base exchanges, to remove subsequences or to add natural or synthetic sequences. To connect the DNA fragments to each other, adaptors or linkers may be attached to the fragments.

For example, plant cells with a reduced activity of a gene product can be generated by expressing at least one corresponding antisense RNA, a sense RNA to achieve a cosuppressory effect or by expressing at least one ribozyme of suitable construction which specifically cleaves transcripts of the abovementioned gene product.

To this end it is possible to make use of, on the one hand, DNA molecules which encompass the entire coding sequence of a gene product inclusive of any flanking sequences which may be present, on the other hand DNA molecules which only encompass parts of the coding sequence, but these parts must be long enough in order to effect, in the cells, an antisense effect. Use may also be made of DNA sequences which show a high degree of homology to the coding sequences of a gene product, but which are not completely identical.

When nucleic acid molecules are expressed in plants, the protein which has been synthesized may be located in any desired compartment of the plant cell. However, to achieve localization in a particular compartment, it is possible, for example, to link the coding region with DNA sequences which guarantee localization in a particular compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J.1 (1991), 95-106).

The transgenic plant cells may be regenerated by known techniques to give complete plants. In principle, the transgenic plants can be plants of any desired plant species, that is to say monocotyledonous and also dicotyledonous plants.

This allows transgenic plants to be obtained which exhibit altered characteristics by means of overexpression, suppression or inhibition of homologous (=natural) genes or gene sequences or by means of expression of heterologous (=foreign) genes or gene sequences.

The Compounds (A) can also be employed in transgenic crops which are resistant to herbicides from the group of the sulfonylureas, imidazolinones, glufosinate-ammonium or glyphosate-isopropylammonium and analogous active substances.

The effects of the Compounds (A) on the useful plants are usually obtained when applying one or more Compounds (A) to the useful plants (seed, growing medium and/or foliage).

The use of the Compounds (A) according to the invention can be accomplished, for instance, by applying the compounds to the locus of the useful plants, for example to the seed, stem, foliage and/or other parts of the plants and/or the growing medium of the plants.

When used as plant growth regulator, for example for promoting root growth or as a culm stabilizer for crop plants like those mentioned above, preferably cereal plants, such as wheat, barley, rye, triticale, millet, rice or corn (maize), the application rate is, for example, in the range of from 0.0001 to 4 kg active substance per hectare of soil surface, preferably in the range of from 0.001 to 2 kg/ha, in particular in the range of from 0.005 to 1500 g/ha of active substance, very particularly from 10 to 1000 g/ha of active substance.

When used as plant growth regulator, for example for promoting root growth the application can be made by the pre-emergence method (pre-sown or similtaneous with sowing, e.g. pre-plant incorporated or in-furrow treatment, or after sowing) or the earyl post-emergence method or later in the post-emergence period, the pre-emergence treatment generally being preferred.

The application as culm stabilizer may take place at various stages of the growth of the plants, generally by the pre-emergence method or the post-emergence method. Preferred is, for example, an application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests. Generally, the application rate of Compound (A) as active substance in case of a seed treatment is from 0.001 to 10 grammes active substance (a. i.) per kilogramme seed, preferably 0.01 to 5 g a. i. per kg seed, in particular 0.1 to 2 g a. i. per kilogramme seed.

If solutions of Compounds (A) are used in the seed treatment method wherein the seeds are soaked in the active substance's solution, the concentration of the active substance (a. i.) in the solution is for example from 1 to 15000 ppm, preferably 10 to 10000 ppm, more preferably 100 to 5000 ppm based on weight.

The plant growth regulator is generally applied in a plant-growth-regulating non-phytotoxic effective amount. By "non-phytotoxic" is meant an amount of the plant growth regulator which causes at most minor or no injury to the desired crop species as regards fruit yield.

The Compounds (A) can be used as stand alone product or in combination with one or more other agrochemicals, preferably a pesticide or other plant-growth regulator, more preferably a pesticide for which the plant growth regulator can effectively be used also as a safener. Of particular interest are combinations of Compounds (A) with herbicides or other plant-growth regulators.

The application rate of the herbicides (B) are in the range used for the herbicides alone and are thus known per se.

Possible combination partners for the inventive active ingredients, in mixed formulations or in a tankmix, are, for example, known active ingredients which are based on inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other usable compounds, with a mechanism of action that is, in some cases, unknown or different, are described, for example, in Weed Research 26, 441-445 (1986), or "The Pesticide Manual", 14th edition 2006/2007, published by the British Crop Protection Council (hereinafter also abbreviated to "PM"), and literature cited there. Herbicides, plant growth regulators and herbicide safeners, which are known from the literature and which can be combined with the compounds of the formula (I), include, for example, the following active ingredients (note: the compounds are either referred to by the common name in accordance with the International Organization for Standardization (ISO) or by the chemical name, if appropriate together with a customary code number): acetochlor; acibenzolar; acibenzolar-S-methyl; acifluorfen; acifluorfen-sodium; aclonifen; alachlor; allidochlor; alloxydim; alloxydim-sodium; ametryn; amicarbazone, amidochlor, amidosulfuron; aminocyclopyrachlor, aminopyralid; amitrole; ammoniumsulfamate; ancymidol; anilofos; asulam; atrazine; azafenidin, azimsulfuron; aziprotryn; BAH-043; BAS-140H, BAS-693H; BAS-714H; BAS-762H; BAS-776H; beflubutamid, benazolin; benazolin-ethyl; bencarbazone; benfluralin; benfuresate; benoxacor; bensulfuron; bensulfuron-methyl; bensulide; bentazone; benzfendizone, benzobicyclon, benzofenap; benzofluor; benzoylprop; benzoylprop-ethyl; bialaphos; bifenox; bilanafos (bialaphos); bilanafos-sodium; bispyribac; bispyribac-sodium, bromacil; bromobutide; bromofenoxim; bromoxynil; bromuron; buminafos; busoxinone; butachlor; butafenacil, butamifos; butenachlor; butralin; butroxydim, butylate; cafenstrole; carbetamide; carfentrazone; carfentrazone-ethyl; chlomethoxyfen; chloramben; chlorazifop; chlorazifop-butyl; chlorbromuron; chlorbufam; chlorfenac; chlorfenac-sodium; chlorfenprop; chlorflurenol; chlorflurenol-methyl; chloridazon; chlorimuron; chlorimuron-ethyl; chlormequat-chloride; chlornitrofen; chlorphthalim; chlorthal-dimethyl; chlorotoluron; chlorpropham; chlorsulfuron; chlorthal-dimethyl; chlorthiamid; chlortoluron, cinidon; cinidon-ethyl, cinmethylin; cinosulfuron; clethodim; clodinafop; clodinafop-propargyl; clofencet; clomazone; clomeprop; cloprop; clopyralid; clopyrasulfuron; clopyrasulfuron-methyl; cloquintocet; cloquintocet-mexyl; cloransulam; cloransulam-methyl, cumyluron; cyanamide, cyanazine; cyclanilide; cycloate; cyclosulfamuron; cycloxydim; cycluron; cyhalofop; cyhalofop-butyl; cyperquat; cyprazine; cyprazole; 2,4-D; 2,4-DB; daimuron (dymron); dalapon; daminozide; dazomet; n-decanol; desmedipham; desmetryn; detosyl-pyrazolate (DTP); di-allate; dicamba; dichlobenil; dichlormid; dichlorprop; dichlorprop-P; diclofop; diclofop-methyl; diclofop-P; diclofop-P-methyl; diclosulam, diethatyl; diethatyl-ethyl; difenoxuron; difenzoquat; diflufenican; diflufenzopyr; diflufenzopyr-sodium; dikegulac-sodium; dimefuron; dimepiperate, dimethachlor; dimethametryn; dimethazone; dimethenamid; dimethenamid-P; dimethipin; dimetrasulfuron; dimexyflam; dinitramine; dinoseb; dinoterb; diphenamid; dipropetryn; diquat; diquat-dibromide; dithiopyr; diuron; DNOC; eglinazine-ethyl; endothal; epoprodan, EPTC; esprocarb; ethalfluralin; ethametsulfuron-methyl; ethephon, ethidimuron; ethiozin; ethofumesate; ethoxyfen; ethoxyfen-ethyl; ethoxysulfuron, etobenzanid; F5231, i.e. N-[2-chloro-4-fluoro-5-[4-(3-fluoropropyl)-4,5-dihydro-5-oxo-1 H-tetrazol-1-yl]phenyl]ethanesulfonamide; fenchlorazole(-ethyl), fenclorim; fenoprop; fenoxan; fenoxaprop; fenoxaprop-ethyl; fenoxaprop-P; fenoxaprop-P-ethyl; fenoxydim; fentrazamide, fenuron; flamprop; flamprop-methyl; flamprop-M-isopropyl; flamprop-M-methyl; flazasulfuron; floazulate, florasulam, fluazifop; fluazifop-butyl; fluazifop-P; fluazifop-P-butyl; fluazolate; flucarbazone; flucarbazone-sodium, flucetosulfuron, fluchloralin; flufenacet (thiafluamide, fluthiamide); flufenpyr; flufenpyr-ethyl; flumetralin, flumetsulam; flumiclorac; flumiclorac-pentyl, flumioxazin; flumipropyn; fluometuron, fluorochloridone, fluorodifen; fluoroglycofen; fluoroglycofen-ethyl; flupoxam; flupropacil; flupropanate; flupyrsulfuron; flupyrsulfuron-methyl-sodium; flurazole; flurenol; flurenol-butyl; fluridone; flurochloridone; fluroxypyr; fluroxypyr-meptyl; flurprimidol, flurtamone; fluthiacet; fluthiacet-methyl; fluthiamide; fluxofenim; fomesafen; foramsulfuron; forchlorfenuron, fosamine; furilazole, furyloxyfen; gibberillic acid; glufosinate; glufosinate-ammonium; glufosinate-P; glufosinate-P-ammonium; glufosinate-sodium; glufosi nate-P-sodium; glyphosate; glyphosate-isopropylammonium; H-9201; halosafen; halosulfuron; halosulfuron-methyl; haloxyfop; haloxyfop-P; haloxyfop-ethoxyethyl; haloxyfop-P-ethoxyethyl; haloxyfop-methyl; haloxyfop-P-methyl; HC-252, hexazinone; HNPC-9908; HW-02; imazamethabenz; imazamethabenz-methyl; imazamox, imazapic, imazapyr; imazaquin; imazamethapyr, imazethapyr; imazosulfuron; inabenfide, indanofan, indole-3-ylacetic acid (IAA), 4-indol-3-ylbutyric acid (IBA); iodosulfuron; iodosulfuron-methyl-sodium; ioxynil; ipfencarbazone; isocarbamid; isopropalin; isoproturon; isouron; isoxaben; isoxachlortole; isoxadifen; isoxadifen-ethyl; isoxaflutole, isoxapyrifop; KUH-043; KUH-071; karbutilate; ketospiradox; lactofen; lenacil; linuron; maleic hydrazide, MCPA; MCPB; MCPB-methyl, -ethyl, and -sodium; mecoprop; mecoprop-sodium; mecoprop-butotyl; mecoprop-P; mecoprop-P-butotyl; mecoprop-P-dimethylammonium; mecoprop-P-2-ethylhexyl; mecoprop-P-potassium; mefenacet; mefenpyr; mefenpyr-diethyl; mefluidide; mepiquat-chloride; mesosulfuron; mesosulfuron-methyl; mesotrione; metam, metamifop, metamitron; metazachlor; methabenzthiazuron; methazole; methoxyphenone; 1-methylcyclopropene; methyldymron; methyl isothiocyanate; metobenzuron; metobromuron; metolachlor; S-metolachlor; metosulam; metoxuron; metribuzin; metsulfuron; metsulfuron-methyl; molinate; monalide; monocarbamide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; 2-(1-naphthyl)acetamide, 1-naphthylacetic acid; 2-naphthyloxyacetic acid; NGGC-011; naproanilide; napropamide; naptalam; NC 310, i.e. 4-(2, 4-dichlorobenzoyl)-1-methyl-5-benzyloxypyrazole; neburon; nicosulfuron; nipyraclofen; nitralin; nitrofen; nitrophenolate-sodium (isomer mixture); nitrofluorfen; nonanoic acid; norflurazon; orbencarb; orthasulfamuron; oryzalin; oxabetrinil; oxadiargyl; oxadiazon; oxasulfuron; oxaziclomefone; oxyfluorfen; paclobutrazol; paraquat; paraquat-dichloride; pebulate; pelargonic acid; pendimethalin; pendralin; penoxsulam; pentachlorophenol; pentanochlor; pentoxazone; perfluidone; pethoxamid, phenisopham; phenmedipham; phenmedipham-ethyl; picloram; picolinafen, pinoxaden, piperophos; piributicarb; pirifenop; pirifenop-butyl; pretilachlor; primisulfuron; primisulfuron-methyl; probenazole; procyazine; prodiamine; profluralin; profoxydim; prohexadione; prohexadione-calcium, prohydrojasmon; prometon; prometryn; propachlor; propanil; propaquizafop; propazine; propham; propisochlor; propoxycarbazone; propoxycarbazone-sodium; n-propyl dihydrojasmonate; propyzamide; prosulfalin; prosulfocarb; prosulfuron; prynachlor; pyraclonil; pyraflufen; pyraflufen-ethyl; pyrasulfotole; pyrazolynate (pyrazolate); pyrazosulfuron; pyrazosulfuron-ethyl; pyrazoxyfen; pyribambenz; pyribambenz-isopropyl; pyribenzoxim; pyributicarb; pyridafol; pyridate; pyriftalid; pyriminobac; pyriminobac-methyl; pyrimisulfan, pyrithiobac; pyrithiobac-methyl; pyrithiobac-sodium (KIH-2031); pyroxasulfone; pyroxsulam; quinclorac; quinmerac; quinoclamine; quinofop and its ester derivatives; quizalofop; quizalofop-ethyl; quizalofop-P; quizalofop-P-ethyl; quizalofop-P-tefuryl; renriduron; rimsulfuron; saflufenacil; secbumeton; sethoxydim; siduron; simazine; simetryn; sintofen; SN 106279, i.e. 2-[[7-[2-chloro-4-(trifluoromethyl)phenoxy]-2-naphthalenyl]oxy] propanoic acid and its methyl ester; sulcotrione; sulfallate (CDEC); sulfentrazone; sulfazuron; sulfometuron; sulfometuron-methyl; sulfosate (glyphosate-trimesium); sulfosulfuron; SYN-449; SYN-523; SYP-249; SYP-298; SYP-300; 2,3,6-TBA; TCA; tebutam; tebuthiuron; tecnazene; tefuryltrione; tembotrione; tepraloxydim; terbacil; terbucarb; terbuchlor; terbumeton; terbuthylazine; terbutryn; TH 547; thenylchlor; thiafluamide; thiazafluron; thiazopyr; thidiazimin; thidiazuron; thiencarbazone; thiencarbazone-methyl; thifensulfuron; thifensulfuron-methyl; thiobencarb; TI-35; tiocarbazil; topramezone; tralkoxydim; tri-allate; triasulfuron; triaziflam; triazofenamide; tribenuron; tribenuron-methyl; trichloroacetic acid (TCA); triclopyr; tridiphane; trietazine; trifloxysulfuron; trifloxysulfuron-sodium; trifluralin; triflusulfuron; triflusulfuron-methyl; trimeturon; trinexapac; trinexapac-ethyl; tritosulfuron; tsitodef; uniconazole; uniconazole-P; vernolate; ZJ-0166; ZJ-0270; ZJ-0862; and the following compounds (see chemical formulae below):

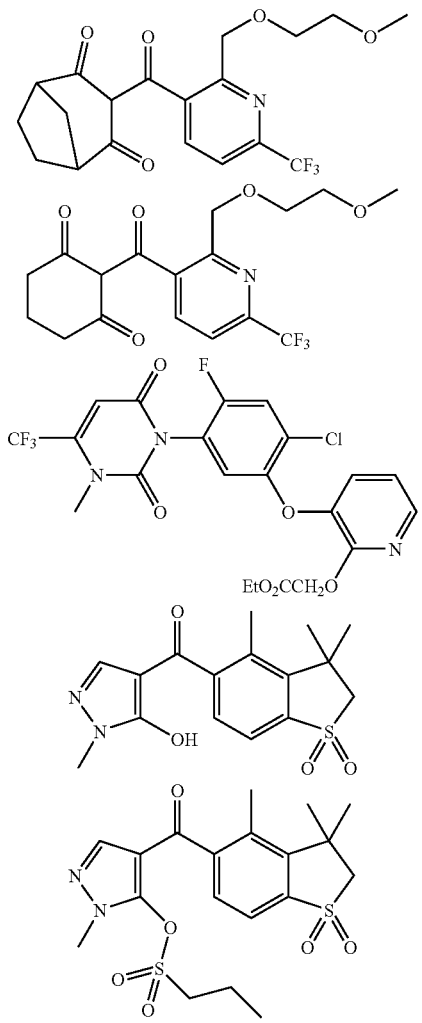

The weight ratio of Compounds (A) to pesticide can be varied within wide limits, and its optimum weight ratio depends both on the Compounds (A) and pesticide employed and on the kind of useful plants to be treated. The ratio by weight of Compounds (A) to pesticide, preferably herbicide, is for example 1000:1 to 1:1000, preferably 200:1 to 1:200, in particular 100:1 to 1:100.

The inventive compounds can be used in the form of agrochemical formulation, such as wettable powders, emulsifiable concentrates, sprayable solutions, dusting products or granules in the customary formulations. The invention therefore also provides plant growth-regulating compositions which comprise Compounds (A) together with formulation auxiliaries.

The Compounds (A) can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie", Volume 7, C. Hanser Verlag Munich, 4th Ed. 1986.

Wettable powders are preparations which can be dispersed uniformly in water and, as well as the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutyinaphthalenesulfonate or else sodium oleylmethyltauride. To prepare the wettable powders, the active herbicidal ingredients are ground finely, for example in customary apparatus such as hammer mills, blower mills and air-jet mills and simultaneously or subsequently mixed with the formulation assistants.

Emulsifiable concentrates are prepared by dissolving the active ingredient in an organic solvent, for example butanol, cyclohexanone, dimethylformamide, xylene or else relatively high-boiling aromatics or hydrocarbons or mixtures of the organic solvents with addition of one or more surfactants of the ionic and/or nonionic type (emulsifiers). The emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely divided solid substances, for example talc, natural clays such as kaolin, bentonite and pyrophyllite, or diatomaceous earth.

Suspension concentrates may be water- or oil-based. They may be prepared, for example, by wet grinding by means of commercial bead mills and optional addition of surfactants as have, for example, already been listed above for the other formulation types.

Emulsions, for example oil-in-water emulsions (EW), can be prepared, for example, by means of stirrers, colloid mills and/or static mixers using aqueous organic solvents and optionally surfactants, as have, for example, already been listed above for the other formulation types.

Granules can be produced either by spraying the active ingredient onto adsorptive granulated inert material or by applying active ingredient concentrates by means of adhesives, for example polyvinyl alcohol, sodium polyacrylate or else mineral oils, onto the surface of carriers such as sand, kaolinites or of granulated inert material. It is also possible to granulate suitable active ingredients in the manner customary for the production of fertilizer granules—if desired in a mixture with fertilizers.

Water-dispersible granules are prepared generally by the customary processes such as spray-drying, fluidized bed granulation, pan granulation, mixing with high-speed mixers and extrusion without solid inert material.

For the preparation of pan, fluidized bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 ff; "Perry's Chemical Engineer's Handbook", 5th Ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active ingredient (Compounds (A) or salts thereof).

In wettable powders, the active ingredient concentration is, for example, from about 10 to 90% by weight; the remainder to 100% by weight consists of customary formulation constituents. In the case of emulsifiable concentrates, the active ingredient concentration may be from about 1 to 90% by weight, preferably from 5 to 80% by weight. Dust-type formulations contain from 1 to 30% by weight of active ingredient, preferably usually from 5 to 20% by weight of active ingredient; sprayable solutions contain from about 0.05 to 80% by weight, preferably from 2 to 50% by weight of active ingredient. In water-dispersible granules, the active ingredient content depends partly on whether the active compound is present in solid or liquid form and which granulation assistants, fillers, etc. are used. In the granules dispersible in water, the content of active ingredient is, for example, between 1 and 95% by weight, preferably between 10 and 80% by weight.

In addition, the active ingredient formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The Compounds (A) or salts thereof may be used as such or in the form of their formulations combined with other pesticidally active substances, for example insecticides, acaricides, nematicides, herbicides, fungicides, safeners, fertilizers and/or growth regulators, for example as a finished formulation or as tankmixes. The combination formulations can be prepared on the basis of the abovementioned formulations (Compounds (A) or salt thereof is then replaced with the combination of Compounds (A) or salt thereof and the active ingredient(s) combined with), while taking account of the physical properties and stabilities of the active ingredients to be combined.

BRIEF DESCRIPTION OF THE DRAWINGS

FIG. 1 depicts active substance treatment in glasshouse pot trial.

FORMULATION EXAMPLES a) A dust is obtained by mixing 10 parts by weight of a Compound (A) or salt thereof and 90 parts by weight of talc as inert substance and commuting the mixture in a hammer mill.
b) A wettable powder which is readily dispersible in water is obtained by mixing 25 parts by weight of a Compound (A) or salt thereof, 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.
c) A readily water-dispersible dispersion concentrate is obtained by mixing 20 parts by weight of a Compound (A) or salt thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.
d) An emulsifiable concentrate is obtained from 15 parts by weight of a Compound (A) or salt thereof, 75 parts by weight of cyclohexanone as solvent and 10 parts by weight of oxethylated nonylphenol as emulsifier.
e) Water-dispersible granules are obtained by mixing
75 parts by weight of a Compound (A) or salt thereof,
10" of calcium lignosulfonate,
5" of sodium lauryl sulfate,
3" of polyvinyl alcohol and
7" of kaolin,
grinding the mixture in a pinned-disk mill, and granulating the powder in a fluidized bed by spraying on water as granulating liquid.
f) Water-dispersible granules are also obtained by homogenizing and precomminuting
25 parts by weight of a Compound (A) or salt thereof,
5" of sodium 2,2'-dinaphthylmethane-6,6'-disulfonate,
2" sodium oleoylmethyltaurate,
1 part by weight of polyvinyl alcohol,
17 parts by weight of calcium carbonate and
50" of water
in a colloid mill, then grinding the mixture in a bead mill, and atomizing and drying the resulting suspension in a spray tower, using a single-fluid nozzle.

BIOLOGICAL EXAMPLES

Example 1

Root Growth Promotion 8 cm round filter papers were placed in 9.5 cm square clear plastic tissue culture containers (ICN Biomedicals, Inc). The paper in each of 4 containers were wetted with 2 ml of tap water containing 2500, 1250 or 625 ppm of cyprosulfamide provided as a 20% wettable powder formulation (WP). 4 further containers were wetted with tap water containing blank WP formulation (i.e. all components except cyprosulfamide). Into each Petri dish 10 seeds of maize (*Zea mays*—variety Oldham) were evenly spread and the lids put in place. The Petri dishes were placed in glasshouse set to 24° C.±2° C. day and 17° C.±2° C. night. High-pressure mercury lamps (400 W) were used to augment daylight during cloudy conditions. As required, small volumes of water were added to the Petri dishes as necessary to keep the filter paper moist. After 13 days the roots from all seeds per container were harvested by cutting as close to the base as possible. The fresh weight of roots was measured immediately. The data was analyzed, and the results are summarized in Table 1 below.

TABLE 1

Effect of Cyprosulfamide on maize root development during germination in a soil free test system

| | Fresh weight (mg) of harvested roots[1] | | | |
|---|---|---|---|---|
| Replicate No. | Blank WP | WP + 625 ppm a.i.[2] | WP + 1250 ppm a.i.[2] | WP + 2500 ppm a.i.[2] |
| 1 | 500 | 547 | 846 | 634 |
| 2 | 278 | 767 | 1087 | 350 |
| 3 | 374 | 587 | 700 | 918 |
| 4 | 115 | 579 | 717 | 1211 |
| Mean | 317 | 620 | 838 | 778 |

Abbreviations and conditions as to Table 1:
WP = formulation auxiliaries of a 20% wettable powder formulation of the active ingredient
[1] = Fresh root weight 13 days after sowing
[2] = concentration of active ingredient cyprosulfamide introduced as 20% wettable powder formulation The results show that the root development of germinating maize seed was significantly enhanced in the presence of cyprosulfamide.

Example 2

Shoot Growth Regulation

Three cyprosulfamide treatment methods (1 to 3) were used in a trial designed to investigate effects on shoot development. Treatment method 1 was a seed treatment. For this, fifty seeds each of two maize varieties (Cecelia and Abraxas) were weighed and placed into each of 50 ml glass screw cap bottles. To one of these bottles sufficient wettable powder formulation of cyprosulfamide (20% formulation) was added to provide 1 g of cyprosulfamide per 1000 g of seed. To the second bottle the same amount of a blank formulation (same components but lacking cyprosulfamide) was added. To each bottle 10 ml of deionised water was added the caps fitted. The bottles were then placed on a shaker for 20 minutes so that the seeds were evenly coated with the formulation.

For methods 2 and 3, 240 peat pots (7 cm diameter) were filled to within 3 cm of the top with steam sterilised sandy-loam soil (20% sand, 57% silt, 23% clay, pH 6.8 and 1.4% organic matter). In addition, 120 Petri dishes (10 cm diameter) were filled (1 cm depth) with the same soil. The 20% wettable powder formulation of cyprosulfamide was dispersed in de-ionised water to produce the required concentration (ppm). 120 pots (Treatment 2) and the all 120 Petri dishes (Treatment 3) were placed on "feed-belt" of a track-sprayer. The spray solution of cyprosulfamide was placed into the spray vessel and applied to the target pots/dishes at a spray volume of 300 l/ha via a flat fan nozzle. This provided a dose rate equivalent to 1000 g of cyprosulfamide per hectare soil surface.

For treatment method 1, five treated maize seed were sown onto 8 replicate untreated pots and covered with untreated soil. For treatment method 2, five untreated seeds were sown onto 8 replicate treated pots and covered with untreated soil. For treatment method 3, five untreated seeds were sown onto 8 replicate untreated pots and covered using the treated soil from the Petri dishes. Control (Treatment 4) had also untreated seeds on untreated soil. The placement of cyprosulfamide as a result of these treatment methods is shown in FIG. 1

All the pots were watered and placed in a glasshouse set to 24° C.±2° C. day and 17° C.±2° C. night. The relative humidity was normally above 60%. High-pressure mercury lamps (400 W) were used to augment daylight during cloudy conditions. Pots were watered as required. 25 days after sowing the height of each plant was measured from soil surface to tip of tallest leaf which was held up against a ruler. The results are summarized in Table 2:

TABLE 2

Effect of treatments on plant height of 2 maize varieties (1 = seed treatment; 2 = soil below seed; 3 = soil above seed; 4 = untreated)

| | Variety | | | | | | | |
|---|---|---|---|---|---|---|---|---|
| | Cecilia | | | | Abraxas | | | |
| | Treatment | | | | | | | |
| | 1 | 2 | 3 | 4 | 1 | 2 | 3 | 4 |
| Replicate | Mean plant height per pot (cm) 25 days after sowing | | | | | | | |
| 1 | 34.3 | 46.0 | 43.0 | 57.5 | 28.2 | 34.2 | 25.2 | 34.8 |
| 2 | 40.7 | 46.0 | 54.0 | 49.2 | 20.8 | 34.5 | 26.6 | 37.2 |
| 3 | 50.0 | 50.0 | 47.6 | 52.2 | 31.6 | 34.4 | 29.6 | 36.2 |
| 4 | 38.3 | 48.2 | 47.0 | 61.4 | 22.6 | 33.4 | 32.2 | 33.6 |
| 5 | 39.3 | 42.8 | 55.5 | 42.3 | 25.2 | 32.2 | 31.4 | 33.0 |
| 6 | 44.0 | 41.7 | 58.0 | 62.7 | 22.2 | 33.6 | 32.2 | 37.4 |
| 7 | 41.0 | 40.6 | 36.8 | 59.8 | 28.8 | 30.5 | 32.8 | 38.8 |
| 8 | 41.7 | 40.3 | 40.8 | 57.2 | 30.6 | 34.6 | 33.0 | 37.3 |
| Mean | 41.2 | 44.4 | 47.8 | 55.3 | 26.3 | 33.4 | 30.4 | 36.0 |

The results show that the height of maize seedlings could be altered by application of cyprosulfamide. Statistical analysis indicated that all treatments significantly reduced plant height in Cecilia and Abraxas.

What is claims is:

1. A method for improving root growth of useful plants, the method comprising:
   applying to the locus of useful plants an effective amount of one or more compounds (Compound (A)) selected from the group consisting of acylsulfonamides of the formula (Ia) or salts thereof:

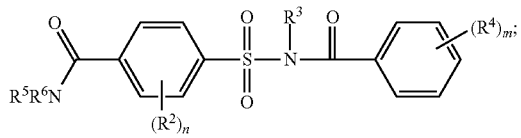

(Ia)

where $R^3$ is hydrogen;
where $(R^4)_m$ is a radical $R^4$ if m is 1 or represents m radicals $R^4$ attached to different carbon ring atoms of the basic ring if m is more than 1, wherein each $R^4$ independently of one another is halogen, methyl, ethyl, n-propyl, i-propyl, $CF_3$, $(C_1-C_4)$haloalkoxy, or $(C_1-C_4)$alkoxy;
where $R^5$ is $(C_1-C_6)$alkyl or $(C_3-C_6)$cycloalkyl, wherein each of the last-mentioned 2 radicals is unsubstituted or substituted by 1, 2 or 3 radicals selected from the group consisting of halogen, $(C_1-C_4)$alkoxy, $(C_1-C_4)$haloalkoxy, $(C_1-C_2)$alkylsulfinyl, $(C_1-C_2)$alkylsulfonyl, $(C_3-C_6)$cycloalkyl, $(C_1-C_4)$alkoxycarbonyl and $[(C_1-C_2)$alkyl$]$carbonyl and, in case of cyclic basic radicals, also $(C_1-C_4)$alkyl, and $(C_1-C_4)$haloalkyl;
where $R^6$ is hydrogen or $(C_1-C_4)$alkyl;
where m is 0, 1, or 2; and
where n is zero;
wherein the seed of the useful plants is treated at an application rate of 0.001 to 10 g of Compound (A) per kg seed.

2. The method according to claim 1;
wherein:
$(R^4)_m$ is 2-methoxy and $R^5$ is cyclopropyl; or
$(R^4)_m$ is 5-chloro-2-methoxy and $R^5$ is cyclopropyl; or
$(R^4)_m$ is 2-methoxy and $R^5$ is ethyl; or
$(R^4)_m$ is 5-chloro-2-methoxy and $R^5$ is isopropyl; or
$(R^4)_m$ is 2-methoxy and $R^5$ is isopropyl; and
wherein:
$R^6$ is hydrogen.

3. The method according to claim 1;
wherein:
$(R^4)_m$ is 2-methoxy;
$R^5$ is cyclopropyl; and
$R^6$ is hydrogen.

4. The method according to claim 1;
wherein the one or more compounds (Compound (A)) are applied so as to increase the root growth of the useful plants regarding total root mass, the average length of roots, the average thickness of roots, the speed of root growth, or secondary roots.

5. The method according to claim 1;
wherein the one or more compounds (Compound (A)) are applied so as to increase yield of the useful plants.

6. The method according to claim 1;
wherein Compound (A) is applied as a stand alone product, optionally in the presence of formulation auxiliaries.

7. The method according to claim 1;
wherein Compound (A) is applied in combination with one or more other agrochemicals, optionally in the presence of formulation auxiliaries.

8. The method according to claim 1;
wherein the useful plants are cereal plants, sugar beet, cotton, sugar cane, soybeans, or plantation crops, plants in fruit production, or viticulture.

9. The method according to claim 1;
wherein the useful plants are plants of wheat, barley, rye, triticale, millet, rice, or maize.

10. The method according to claim 1;
wherein the useful plants are plants of maize.

11. The method according to claim 1;
wherein:
$R^6$ is hydrogen; and
m is 1 or 2.

12. A method for increasing root growth of useful plants, the method comprising:
applying to the locus of useful plants an effective amount of one or more compounds (Compound (A)) selected from the group consisting of an acylsulfonamide of the formula (Ia) or salts thereof:

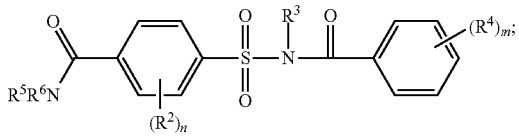

(Ia)

where $R^3$ is hydrogen;
where $R^4$ is 2-methoxy;
where $R^5$ cyclopropyl;
where $R^6$ is hydrogen;
where m 1; and
where n is zero;
wherein the one or more compounds (Compound (A)) are applied so as to improve root growth of useful plants as compared to regular root growth; and
wherein the seed of the useful plants is treated at an application rate of 0.001 to 10 g of Compound (A) per kg seed.

13. The method according to claim 12;
wherein one or more compounds (Compound (A)) are applied so as to increase the root growth of the useful plants regarding total root mass, the average length of roots, the average thickness of roots, the speed of root growth, or secondary roots.

14. The method according to claim 12;
wherein the one or more compounds (Compound (A)) are applied so as to increase yield of the useful plants.

15. The method according to claim 12;
wherein Compound (A) is applied as a stand alone product, optionally in the presence of formulation auxiliaries.

16. The method according to claim 12;
wherein the useful plants are cereal plants, sugar beet, cotton, sugar cane, soybeans, or plantation crops, plants in fruit production, or viticulture.

17. The method according to claim 12;
wherein the useful plants are plants of wheat, barley, rye, triticale, millet, rice, or maize.

18. The method according to claim 12;
wherein the useful plants are plants of maize.

19. The method according to claim 1;
wherein the seed of the useful plants is treated a solution comprising the Compound (A) in a concentration of more than 625 ppm to 15,000 ppm.

20. The method according to claim 19;
wherein the seed of the useful plants is treated a solution comprising the Compound (A) in a concentration of more than 1,000 ppm to 15,000 ppm.

21. The method according to claim 20;
wherein the seed of the useful plants is treated a solution comprising the Compound (A) in a concentration of more than 10,000 ppm to 15,000 ppm.

* * * * *